United States Patent [19]

Böckmann et al.

[11] Patent Number: 4,921,528
[45] Date of Patent: May 1, 1990

[54] SUBSTITUTED AZOLYLMETHYL-CYCLOPROPYL-CARBINOL DERIVATIVES

[75] Inventors: Klaus Böckmann, Cologne; Erik Regel, Wuppertal; Karl H. Büchel, Burscheid; Klaus Lürssen, Bergisch Gladbach; Jörg Konze, Cologne; Wilhelm Brandes, Leichlingen, all of Fed. Rep. of Germany

[73] Assignee: Bayer Aktiengesellschaft, Leverkusen, Fed. Rep. of Germany

[21] Appl. No.: 260,212

[22] Filed: Oct. 19, 1988

Related U.S. Application Data

[63] Continuation of Ser. No. 792,088, Oct. 28, 1985, abandoned.

[30] Foreign Application Priority Data

Nov. 2, 1984 [DE] Fed. Rep. of Germany ....... 3440116
Jun. 22, 1985 [DE] Fed. Rep. of Germany ....... 3522440
Sep. 26, 1985 [DE] Fed. Rep. of Germany ....... 3534310

[51] Int. Cl.$^5$ ................. A01N 43/653; C07D 249/08
[52] U.S. Cl. .......................................... 71/92; 71/76;
71/88; 71/94; 514/184; 514/383; 514/326;
514/236.2; 514/255; 544/132; 544/366;
546/210; 548/101; 548/267.8

[58] Field of Search ............... 548/101, 262; 514/184,
514/383, 255, 326, 236.2; 71/76, 92, 88, 94;
546/210; 544/366, 132

[56] References Cited

U.S. PATENT DOCUMENTS

| | | | |
|---|---|---|---|
| 4,432,989 | 2/1984 | Spencer | 548/341 |
| 4,551,469 | 11/1985 | Parry et al. | 514/383 |
| 4,595,406 | 6/1986 | Parry et al. | 71/76 |
| 4,664,696 | 5/1987 | Schaub | 548/262 |
| 4,715,887 | 12/1987 | Kramer et al. | 71/92 |

FOREIGN PATENT DOCUMENTS

| | | | |
|---|---|---|---|
| 0044605 | 1/1982 | European Pat. Off. | 548/262 |
| 054974 | 6/1982 | European Pat. Off. | 548/341 |
| 070798 | 1/1983 | European Pat. Off. | 548/262 |
| 086173 | 8/1983 | European Pat. Off. | 548/262 |
| 106515 | 9/1983 | European Pat. Off. | 548/262 |
| 111234 | 6/1984 | European Pat. Off. | 548/262 |
| 2535321 | 5/1984 | France | 548/262 |
| 2129000 | 5/1984 | United Kingdom | 548/262 |
| 2136423 | 9/1984 | United Kingdom | 548/262 |

OTHER PUBLICATIONS

Okuma et al., "Reaction of Dimethyloxosulfonium, etc.", *JOC*, 48, (1983), pp. 5133–5134.

*Primary Examiner*—Glennon H. Hollrah
*Assistant Examiner*—Patricia L. Morris
*Attorney, Agent, or Firm*—Sprung Horn Kramer & Woods

[57] ABSTRACT

Plant growth-regulating and fungicidal compounds of the formula

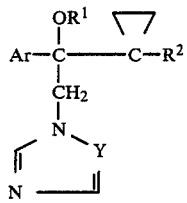

in which

Ar represents optionally substituted aryl or optionally substituted heteroaryl, $R^1$ represents hydrogen, alkyl, alkenyl, alkynyl, trialkylsilyl, optionally substituted phenylalkyl or an acyl radical, $R^2$ represents halogen, cyano, thiocyano, alkylcarbonyloxy, alkylcarbonylthio or the groupings $-X-R^3$ and $-NR^4R^5$, $R^3$ represents alkyl, cycloalkyl, alkenyl, alkynyl, hydroxyalkyl, alkylthioalkyl, carboxyalkyl, alkoxycarbonylalkyl, optionally substituted aryl, optionally substituted aralkyl or the radical of the formula

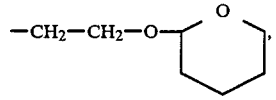

$R^4$ and $R^3$ independently of one another represent hydrogen or alkyl, or $R^4$ and $R^5$, together with the nitrogen atom to which they are bonded, represent an optionally substituted cycloaliphatic ring which can contain further heteroatoms, X represents oxygen, sulphur, an SO group or an $SO_2$ group, or $R^2$ furthermore represents hydrogen when Ar represents optionally substituted heteroaryl, and Y represents nitrogen or a CH group, or addition products thereof with acids or metal salts. Novel intermediates are also shown.

5 Claims, No Drawings

SUBSTITUTED AZOLYLMETHYL-CYCLOPROPYL-CARBINOL DERIVATIVES

This is a continuation of application Ser. No. 792,088, filed Oct. 28, 1985, now abandoned.

The present invention relates to new substituted azolylmethyl-cyclopropyl-carbinol derivatives, several processes for their preparation and their use as plant growth regulators and fungicides.

It has already been disclosed that certain diazolyl derivatives possess fungicidal and plant growth regulating properties (see EP-OS (European Published Specification) No. 0,044,605). Thus, for example, 1,3-di-(1,2,4-triazol-1-yl)-2-(2-chlorophenyl)-propan-2-ol, 1,3-di-(1,2,4-triazol-1-yl)-2-(3-chlorophenyl)-propan-2-ol, 1,3-di-(1,2,4-triazol-1-yl)-2-(4-chlorophenyl)-propan-2-ol and 1,3-di-(1,2,4-triazol-1-yl)-2-phenyl-propan-2-ol can be used for regulating plant growth and for combating fungi. However, the action of these substances is not always completely satisfactory, particularly when small amounts and concentrations are used.

New substituted azolylmethyl-cyclopropyl-carbinol derivatives of the formula

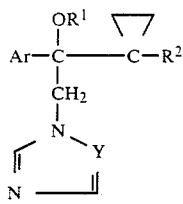

in which

Ar represents optionally substituted aryl or optionally substituted heteroaryl, $R^1$ represents hydrogen, alkyl, alkenyl, alkinyl, trialkylsilyl, optionally substituted phenylalkyl or an acyl radical, $R^2$ represents halogen, cyano, thiocyano, alkylcarbonyloxy, alkylcarbonylthio or the groupings —X—$R^3$ and —N$R^4R^5$ wherein $R^3$ represents alkyl, cycloalkyl, alkenyl, alkinyl, hydroxyalkyl, alkylthioalkyl, carboxyalkyl, alkoxycarbonylalkyl, optionally substituted aryl, optionally substituted aralkyl or the radical of the formula

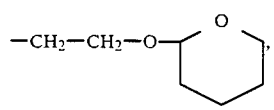

$R^4$ and $R^5$ independently of one another represent hydrogen or alkyl, or $R^4$ and $R^5$, together with the nitrogen atom to which they are bonded, represent an optionally substituted cycloaliphatic ring which can contain further heteroatoms, X represents oxygen, sulphur, an SO group or an $SO_2$ group, and $R^2$ furthermore represents hydrogen when Ar represents optionally substituted heteroaryl, and Y represents nitrogen or a CH group, and their acid addition salts and metal salt complexes have now been found.

Furthermore, it has been found that substituted azolylmethyl-cyclopropyl-carbinol derivatives of the formula (I) and their acid addition salts and metal salt complexes are obtained when (a) in a first stage, aryl cyclopropyl ketones of the formula

in which

Ar and $R^2$ have the meaning given above, are reacted with dimethyloxosulphonium methylide of the formula $$(CH_3)_2{}^{\delta+}SO^{\delta-}CH_2$$

in the presence of a diluent, and, in a second stage, the resulting aryl-cyclopropyl-oxiranes of the formula

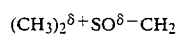

in which

Ar and $R^2$ have the meaning given above, are reacted with azoles of the formula

in which

Y has the meaning given, in the presence of a diluent and in the presence of a base, or (b) azolylketo compounds of the formula

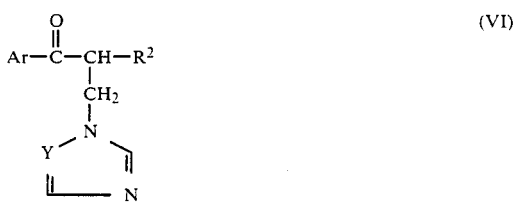

in which $R^2$, Ar and Y have the meaning given above, are reacted with dimethyloxosulphonium methylide of the formula

in the presence of a diluent, or (c) azolylmethyl-thio-cyclopropyl-carbinol derivatives of the formula

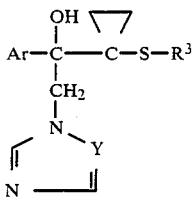

(Ia)

in which
Ar, R³ and Y have the meaning given above,
are reacted with oxidizing agents, if appropriate in the presence of a diluent, or
(d) hydroxy compounds of the formula

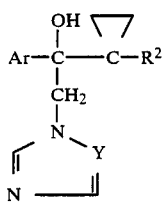

(Ib)

in which
Ar, R² and Y have the meaning given above,
are reacted with strong bases in the presence of a diluent, and the resulting alcoholates of the formula

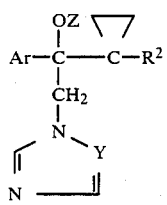

(Ic)

in which
Ar, R² and Y have the meaning given above and
Z represents a base radical,
are reacted with a halogen compound of the formula R—Hal (VII)

in which
R represents alkyl, alkenyl, alkinyl, trialkylsilyl, optionally substituted phenylalkyl or an acyl radical, and
Hal represents halogen,
in the presence of a diluent; and, if appropriate, the compounds of the formula (I) which are obtained in this manner are then subjected to an addition reaction with an acid or a metal salt.

Finally, it has been found that the new substituted azolylmethyl-cyclopropyl-carbinol derivatives of the formula (I) and their acid addition salts and metal salt complexes possess powerful plant growth regulating and fungicidal properties.

Surprisingly, the substances according to the invention exhibit a better plant growth-regulating and fungicidal activity than the constitutionally similar diazolyl derivatives 1,3-di-(1,2,4-triazol-1-yl)-2-(2-chlorophenyl)-propan-2-ol, 1,3-di-(1,2,4-triazol-1-yl)-2-(3-chlorophenyl)-propan-2-ol, 1,3-di-(1,2,4-triazol-1-yl)-2-(4-chlorophenyl)-propan-2-ol and 1,3-di-(1,2,4-triazol-1-yl)-2-phenyl-propan-2-ol which are known from the prior art and can be used for the same indications.

Formula (I) gives a general definition of the substituted azolylmethyl-cyclopropane-carbinol derivatives according to the invention. In this formula Ar preferably represents phenyl which is optionally monosubstituted or polysubstituted by identical or different substituents, preferred substituents being: halogen; alkyl, alkoxy and alkylthio, each having 1 to 4 carbon atoms; halogenoalkyl, halogenoalkoxy and halogenoalkylthio, each having 1 or 2 carbon atoms and 1 to 5 identical or different halogen atoms, such as fluorine atoms and chlorine atoms; and phenyl or phenoxy, each of which is optionally substituted by alkyl having 1 or 2 carbon atoms and/or halogen; and furthermore represents naphthyl and a 5-membered or 6-membered heteroaromatic which is optionally monosubstituted or polysubstituted by identical or different substituents and contains nitrogen, oxygen and/or sulphur as heteroatoms, preferred substituents being the abovementioned phenyl substituents;

$R^1$ preferably represents hydrogen, straight-chain or branched alkyl having 1 to 4 carbon atoms, straight-chain or branched alkenyl and alkinyl, each having 2 to 4 carbon atoms, trialkylsilyl having 1 to 4 carbon atoms in each alkyl part, alkylcarbonyl having 1 to 4 carbon atoms in the alkyl part, and phenylalkyl which has one or two carbon atoms in the alkyl part and is optionally monosubstituted or polysubstituted by identical or different substituents, preferred substituents being the phenyl substituents already mentioned for Ar, $R^2$ preferably represents fluorine, chlorine, bromine, cyano, thiocyano, alkylcarbonyloxy having 1 to 4 carbon atoms in the alkyl part, alkylcarbonylthio having 1 to 4 carbon atoms in the alkyl part, or the groupings —X—$R^3$ and —$NR^4R^5$,
wherein
$R^3$ preferably represents straight-chain or branched alkyl having 1 to 18 carbon atoms, cycloalkyl having 3 to 8 carbon atoms, straight-chain or branched alkenyl having 2 to 18 carbon atoms, straight-chain or branched alkinyl having 2 to 18 carbon atoms, hydroxyalkyl having 1 to 18 carbon atoms, alkylthioalkyl having 1 to 6 carbon atoms in the alkylthio part and 1 to 6 carbon atoms in the alkyl part, carboxyalkyl having 1 to 18 carbon atoms in the alkyl part, alkoxycarbonylalkyl having 1 to 6 carbon atoms in the alkoxy part and 1 to 6 carbon atoms in the alkyl part, and phenyl or phenylalkyl having 1 or 2 carbon atoms in the alkyl part, each of which is optionally monosubstituted or polysubstituted by identical or different substituents, preferred substituents in each case being the phenyl substituents mentioned as being preferred for Ar or $R^3$ represents the radical of the formula

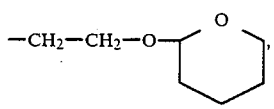

$R^4$ and $R^5$ independently of one another preferably represent hydrogen or straight-chain or branched alkyl having 1 to 4 carbon atoms, or $R^4$ and $R^5$, together with the nitrogen atom to which they are bonded, preferably represent a 5-membered or 6-membered ring which is optionally substituted by alkyl having 1 to 4 carbon atoms or alkylcarbonyl having 1 to 4 carbon atoms in the alkyl part, and can contain oxygen, sulphur and/or nitrogen as further heteroatoms, and X preferably represents oxygen, sulphur, an SO group or an $SO_2$ group, and $R^2$ furthermore represents hydrogen when Ar represents an optionally substituted 5-membered or 6-membered heteroaromatic, and Y preferably represents nitrogen or a CH group.

Particularly preferred compounds of the formula (I) are those in which

Ar represents phenyl which is optionally monosubstituted to trisubstituted, in particular monosubstituted or disubstituted, by identical or different substituents, the following being mentioned as substituents: fluorine, chlorine, methyl, isopropyl, tert.-butyl, methoxy, methylthio, trifluoromethyl, trifluoromethoxy, trifluoromethylthio, and phenyl or phenoxy, each of which is optionally substituted by fluorine, chlorine and/or methyl; and furthermore represents naphthyl, and represents furyl, thienyl, pyridinyl or pyrimidinyl, each of which is optionally monosubstituted or disubstituted by identical or different substituents, suitable substituents being the abovementioned phenyl substituents;

$R^1$ represents hydrogen, methyl, ethyl, n-propyl, isopropyl, n-butyl, isobutyl, allyl, propargyl, trimethylsilyl, methylcarbonyl, ethylcarbonyl, n-propylcarbonyl, isopropylcarbonyl, n-butylcarbonyl, isobutylcarbonyl, and benzyl which is optionally monosubstituted to trisubstituted, in particular monosubstituted or disubstituted, by identical or different substituents, preferred substituents being the phenyl substituents already mentioned as being preferred for Ar, $R^2$ represents fluorine, chlorine, bromine, cyano, thiocyano, methylcarbonyloxy, ethylcarbonyloxy, n-propylcarbonyloxy, isopropylcarbonyloxy, n-butylcarbonyloxy, isobutylcarbonyloxy, methylcarbonylthio, ethylcarbonylthio, n-propylcarbonylthio, isopropylcarbonylthio, n-butylcarbonylthio, isobutylcarbonylthio or the groupings —X—$R^3$ or —N$R^4R^5$, wherein $R^3$ represents straight-chain or branched alkyl having 1 to 12 carbon atoms, straight-chain or branched alkenyl having 2 to 12 carbon atoms, straight-chain or branched alkinyl having 2 to 12 carbon atoms, hydroxyalkyl having 1 to 12 carbon atoms, carboxyalkyl having 1 to 12 carbon atoms in the alkyl part, alkoxycarbonylalkyl having 1 to 4 carbon atoms in the alkoxy part and 1 to 4 carbon atoms in the alkyl part, and phenyl or benzyl, each of which is optionally monosubstituted to trisubstituted, in particular monosubstituted or disubstituted, by identical or different substituents, suitable substituents being the phenyl substituents already mentioned above for Ar as being particularly preferred, $R^4$ and $R^5$ independently of one another represent hydrogen, methyl, ethyl, n-propyl, isopropyl, n-butyl or isobutyl, or $R^4$ and $R^5$ together with the nitrogen atom to which they are bonded, represent piperidinyl, piperazinyl or morpholinyl each of which is optionally substituted by methyl, ethyl, methylcarbonyl or ethylcarbonyl, and X represents oxygen, sulphur, and SO group or an $SO_2$ group, and furthermore $R^2$ also represents hydrogen when Ar represents one of the abovementioned optionally substituted heteroaromatics, and Y represents nitrogen or a CH group.

Other preferred compounds according to the invention are addition products of acids and those substituted azolylmethyl-cyclopropyl-carbinol derivatives of the formula (I) in which Ar, $R^1$, $R^2$ and Y have the meanings which have already been mentioned as being preferred for these radicals.

The acids which can be used for addition reactions preferably include hydrohalic acids, such as, for example, hydrochloric acid and hydrobromic acid, in particular hydrochloric acid, and furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acid, such as, for example, p-toluenesulphonic acid, naphthalene-1,5-disulphonic acid or camphorsulphonic acid.

Other preferred compounds according to the invention are addition products of salts of metals of main groups II to IV and subgroups I and II and IV to VIII of the periodic table and those substituted azolylmethyl-cyclopropyl-carbinol derivatives of the formula (I), in which Ar, $R^1$, $R^2$ and Y have the meanings which have already been mentioned as being preferred for these radicals. In this context, salts of copper, zinc, manganese, magnesium, tin, iron and nickel are particularly preferred. Suitable anions of these salts are those which are derived from acids which lead to physiologically tolerated addition products. Particularly preferred acids of this type in this context are the hydrohalic acids, such as, for example, hydrochloric acid and hydrobromic acid, and furthermore phosphoric acid, nitric acid and sulphuric acid.

If, for example, 1-(4-chlorobenzoyl)-1-ethylthiocyclopropane and dimethyloxosulfonium methylide are used as starting materials, and 1,2,4-triazole is used as a reactant, the course of process (a) according to the invention can be represented by the following equation:

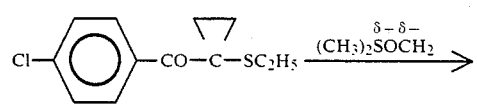

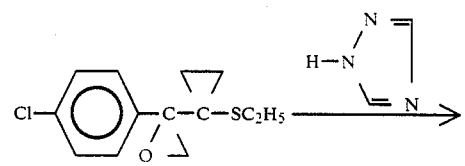

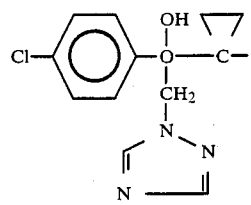
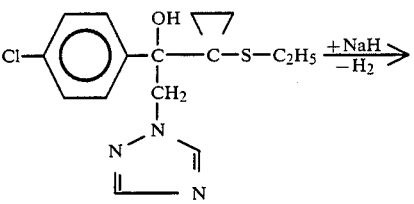

If, for example, 1-(4-chlorophenoxy)-2-(1,2,4-triazol-1-yl)-propiophenone and dimethyloxosulphonium methylide are used as starting materials, the course of process (b) according to the invention can be represented by the following equation:

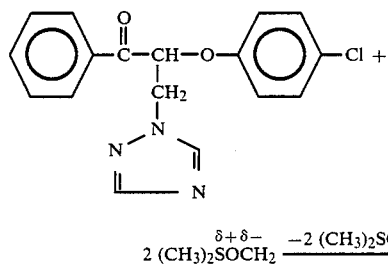

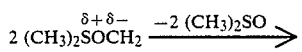

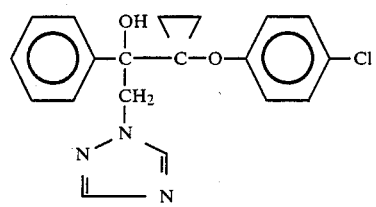

If, for example, 1-(4-chlorophenyl)-1-[1-(ethylthio)-1-cyclopropyl]-2-(1,2,4-triazol-1-yl)-1-ethanol and hydrogen peroxide in glacial acetic acid are used as starting materials, the course of process (c) according to the invention can be represented by the following equation:

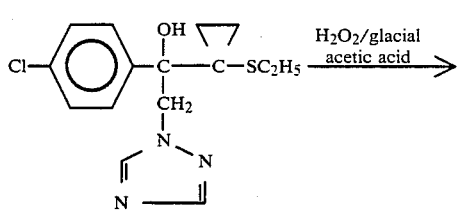

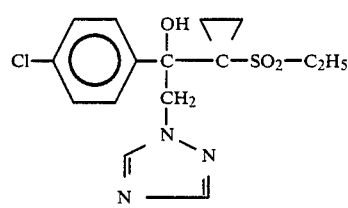

If, for example, 1-(4-chlorophenyl)-1-([1-(ethylthio)-1-cyclopropyl]-2-(1,2,4-triazol-1-yl)-1-ethanol and sodium hydride are used as starting materials, and iodomethane is used as a reactant, the course of process (d) according to the invention can be represented by the following equation:

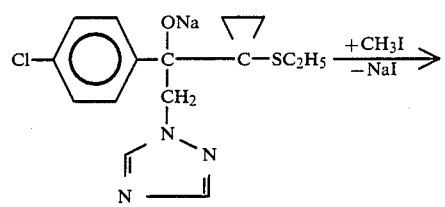

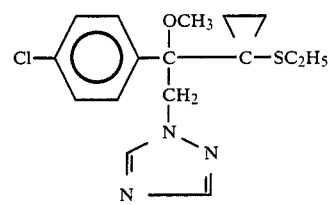

Formula (II) gives a general definition of the aryl cyclopropyl ketones to be used as starting materials for process (a) according to the invention. In this formula, Ar and $R^2$ preferably have the meanings which have already been mentioned in connection with the description of the substances according to the invention, of the formula (I), as being preferred for these substituents.

The aryl cyclopropyl ketones of the formula (II) were hitherto unknown. They can be prepared by a method in which aryl halogenopropyl ketones of the formula $$Ar-CO-CH-CH_2CH_2-Hal'' \quad (VIII)$$
$$| \quad \quad \quad \quad \quad \quad \quad \quad \quad Hal'$$

in which
  Ar has the meaning given above,
  Hal' represents halogen and
  Hal'' represents bromine or chlorine,
(α) are reacted with compounds of the formula $$HR^6 \quad (IX)$$

in which
  $R^6$ represents cyano, thiocyano, alkylcarbonyloxy, alkylcarbonyl-thio or the groupings —X $R^3$ and —NR$^4$R$^5$,
wherein
  $R^3$ represents alkyl, cycloalkyl, alkenyl, alkinyl, hydroxyalkyl, alkylthioalkyl, carboxyalkyl, alkoxycarbonylalkyl, optionally substituted aryl, optionally substituted aralkyl or the radical of the formula

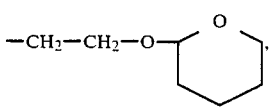

R[4] and R[5] independently of one another represent hydrogen or alkyl, or

R[4] and R[5], together with the nitrogen atom to which they are bonded, represent an optionally substituted cycloaliphatic ring which can contain further heteroatoms, and X represents oxygen, sulphur, an SO group or an SO[2] group, in the presence of a diluent and in the presence of a base, or (β) are heated directly in the presence of a diluent and in the presence of a base.

In the compounds of the formula (VIII), Ar preferably has the meanings which have already been mentioned in connection with the description of the substances according to the invention, of the formula (I), as being preferred for Ar. Hal' preferably represents fluorine, chlorine or bromine and Hal" preferably represents chlorine or bromine.

The aryl halogenopropyl ketones of the formula (VIII) are known, or can be prepared in a simple manner by processes which are known in principle (see DE-OS (German Published Specification) No. 2,521,104, DE-OS (German Published Specification) No. 2,320,355 and DE-OS (German Published Specification) No. 2,351,948). Thus, for example, the aryl halogenopropyl ketones of the formula (VIII) in which Hal' represents fluorine can be prepared by reacting the corresponding compounds of the formula (VIII), in which Hal' represents bromine, with alkali metal fluorides, such as sodium fluoride or potassium fluoride, in the presence of an inert organic diluent, such as, for example, benzene, and in the presence of a macrocyclic ether, such as, for example, 18-crown-6 (see preparation examples).

In the compounds of the formula (IX),

R[6] preferably represents cyano, thiocyano, alkylcarbonyloxy having 1 to 4 carbon atoms in the alkyl part, alkylcarbonylthio having 1 to 4 carbon atoms in the alkyl part, or the groupings —XR[3] and —NR[4]R[5], in which R[3], R[4], R[5] and X preferably have those meanings which have already been mentioned in connection with the description of the substances according to the invention, of the formula (I), as being preferred for these radicals.

The compounds of the formula (IX) are known, or can be prepared by methods which are known in principle.

If the above process for the preparation of aryl cyclopropyl ketones of the formula (II) is carried out by method (β), the compounds of the formula (II) which are obtained are those in which R[2] represents halogen.

In the above process the preparation of the aryl cyclopropyl ketones of the formula (II), suitable diluents for the procedure according to variant (α) as well as that according to variant (β) are all organic solvents which are inert under the reaction conditions. Solvents which are preferably used are alcohols, such as methanol, ethanol, methoxyethanol, propanol or tert.-butanol, as well as ketones, such as acetone and 2-butanone, nitriles, such as acetonitrile, esters, such as ethyl acetate, ethers, such as dioxane, aromatic hydrocarbons, such as benzene or toluene, and amides, such as dimethylformamide.

Suitable bases for the preparation of aryl cyclopropyl ketones of the formula (II), both in the procedure according to variant (α) and in that according to variant (β), are all inorganic and organic bases which are usually employed. These preferably include alkali metal carbonates such as sodium carbonate and potassium carbonate, alkali metal hydroxides, such as sodium hydroxide and potassium hydroxide, alkali metal alcoholates, such as sodium methylate, sodium ethylate, sodium tert.-butylate, potassium methylate, potassium ethylate and potassium tert.-butylate; alkali metal hydrides, such as sodium hydride, and lower tertiary alkylamines, such as cycloalkylamines and aralkylamines, such as, in particular, triethylamine.

In carrying out the above process for the preparation of the aryl cyclopropyl ketones of the formula (II), the reaction temperatures can be varied within a relatively wide range, both in variant (α) and in variant (β). In general, the reactions are carried out at temperatures between 0° C. and 200° C., preferably between 20° C. and 150° C.

In the preparation of aryl cyclopropyl ketones of the formula (II) by the above process variant (α), 1 to 2 mols of the compound of the formula (IX) and 1 to 2 mols of a base are preferably employed per mol of the aryl halogenopropyl ketone of the formula (VIII). The compounds of the formula (II) are isolated in a customary manner.

The aryl cyclopropyl ketones of the formula (II) are not only of interest as starting materials for the preparation of the compounds according to the invention, of the formula (I), but furthermore constitute valuable intermediate products for the synthesis of other substances.

The dimethyloxosulphonium methylide of the formula (III) which is required as a reactant in processes (a) and (b) according to the invention is known (see J. Am. Chem. Soc. 87, 1363–1364 (1965)). In the above reaction, it is processed in the freshly prepared state, by producing it in situ by reacting trimethyloxosulphonium iodide with sodium hydride or sodium amide, in particular with potassium tert.-butylate or sodium methylate, in the presence of a diluent.

The azoles of the formula (V) which are furthermore required for the second stage of process (a) according to the invention, are generally known compounds of organic chemistry.

The aryl-cyclopropyl-oxiranes of the formula (IV) which occur as intermediate products in process (a) according to the invention were hitherto unknown. They constitute intermediate products of general interest.

Formula (VI) gives a general definition of the azolyl-keto compounds to be used as starting materials for process (b) according to the invention. In this formula (VI), R[2], Ar and Y preferably represent those radicals which have already been mentioned in connection with the description of the substances according to the invention, of the formula (I), as being preferred for these substituents.

Only some of the azolyl-keto compounds of the formula (VI) were known hitherto (see DE-OS (German Published Specification) No. 2,348,663).

The azolyl-keto compounds of the formula

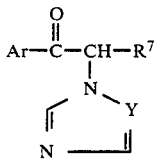

in which
Ar represents optionally substituted aryl or optionally substituted heteroaryl,
Y represents nitrogen or a CH group and
$R^7$ represents halogen, cyano, thiocyanato, alkylcarbonyloxy, alkylcarbonylthio or the groupings $-X-R^8$ and $-NR^4R^5$,
wherein
X represents oxygen, sulphur, or an SO or $SO_2$ group,
$R^8$ represents alkyl, cycloalkyl, alkenyl, alkinyl, hydroxyalkyl, alkylthioalkyl, carboxyalkyl, alkoxycarbonylalkyl optionally substituted aralkyl or the radical of the formula

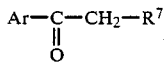

$R^4$ and $R^5$ independently of one another represent hydrogen or alkyl, or
$R^4$ and $R^5$, together with the nitrogen atom to which they are bonded, represent an optionally substituted cycloaliphatic ring which can contain further heteroatoms, and
$R^7$ also represents hydrogen when Ar represents optionally substituted heteroaryl,
are new.

The azolyl-keto compounds of the formula (VIa) can be prepared by a method in which ketones of the formula

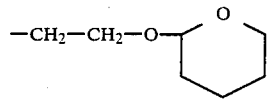 (X)

in which
Ar and $R^7$ have the above meaning,
are reacted with hydroxymethylazoles of the formula

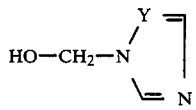 (XI)

in which
Y has the meaning given above,
in the presence of a diluent and in the presence of a catalyst.

In the azolyl-keto compounds of the formula (VIa), Ar and Y preferably have those meanings which have already been mentioned in connection with the description of the substances according to the invention, of the formula (I), as being preferred for these radicals. $R^7$ preferably represents fluorine, chlorine, bromine, cyano, thiocyano, alkylcarbonyloxy having 1 to 4 carbon atoms in the alkyl part, alkylcarbonylthio having 1 to 4 carbon atoms in the alkyl part, or the groupings $-XR^8$ and $-NR^4R_5$, in which
X preferably represents oxygen, sulphur, an SO group or an $SO_2$ group,
$R^8$ preferably represents straight-chain or branched alkyl having 1 to 18 carbon atoms, cycloalkyl having 3 to 8 carbon atoms, straight-chain or branched alkenyl having 2 to 18 carbon atoms, straight-chain or branched alkinyl having 2 to 18 carbon atoms, alkylthioalkyl having 1 to 6 carbon atoms in the alkylthio part and 1 to 6 carbon atoms in the alkyl part, carboxyalkyl having 1 to 18 carbon atoms in the alkyl part, alkoxycarbonylalkyl having 1 to 6 carbon atoms in the alkoxy part and 1 to 6 carbon atoms in the alkyl part, and phenylalkyl which has 1 or 2 carbon atoms in the alkyl part and is optionally monosubstituted or polysubstituted by identical or different substituents, preferred substituents being the phenyl substituents mentioned as being preferred for Ar, or $R^8$ represents the radical of the formula

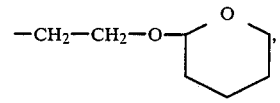

and
$R^4$ and $R^5$ preferably have the meanings which have already been mentioned in connection with the description of the substances according to the invention, of the formula (I), as being preferred for these radicals, and furthermore
$R^7$ preferably represents hydrogen when Ar represents an optionally substituted 5-membered or 6-membered heteroaromatic.

The ketones of the formula (X) which are required as starting materials in the preparation of the arylketo compounds of the formula (VIa) are known or can be prepared by methods which are known in principle.

The hydroxymethylazoles of the formula (XI), which are furthermore required as starting materials in the preparation of the aryl-keto compounds of the formula (VIa) by the above process, are known (see EP-OS (European Published Specification) No. 0,006,102 and Chem. Heterocycl. Comp. 1980, 189).

Preferred diluents for the above process for the preparation of the azolyl-keto derivatives of the formula (VIa) are inert organic solvents. These preferably include alcohols, such as methanol, and phenol, as well as ethers, such as tetrahydrofuran and dioxane, aromatic hydrocarbons, such as benzene and toluene, and halogenated aliphatic and aromatic hydrocarbons, such as methylene chloride, chloroform, chlorobenzene and dichlorobenzene.

The process for the preparation of the azolyl-keto derivatives of the formula (VIa) is carried out in the presence of a catalyst. In this process, it is possible to employ all acidic and, in particular, basic catalysts which are customarily used, and their buffer mixtures. These preferably include Lewis acids, such as, for example, boron trifluoride, boron trichloride, tin tetrachloride or titanium tetrachloride; organic bases, such as pyridine and piperidine, and in particular piperidine acetate.

In carrying out this process, the reaction temperatures can be varied within a relatively wide range. In general, the reaction is carried out at between 20° and 160° C., preferably at the boiling point of the particular solvent.

In carrying out this process, 1 to 1.5 mol of the hydroxymethylazole of the formula (XI) and catalytic to 0.2 molar amounts of catalyst are employed per mol of the ketone of the formula (X).

The azolyl-keto derivatives of the formula (VI) constitute interesting intermediate products and also exhibit fungicidal and plant growth-regulating properties when used in appropriate amounts or concentrations.

The azolylmethyl-thiocyclopropyl-carbinol derivatives of the formula (Ia) to be used as starting materials for process (c) according to the invention, are compounds according to the invention.

Suitable reactants for process (c) according to the invention are all oxidising agents customarily used for such reactions. Hydrogen peroxide and per acids, such as m-chloroperbenzoic acid and peracetic acid, are preferably used.

The hydroxy compounds of the formula (Ib) to be used as starting materials for process (d) according to the invention are likewise compounds according to the invention. Their conversion to the corresponding alcoholates is carried out in a generally known manner by reaction with suitable strong bases, such as alkali metal amides or hydrides, quaternary ammonium hydroxides or phosphonium hydroxides, in an inert solvent, such as, for example, dioxane, at room temperature.

Accordingly, in the compounds of the formula (Ic), Z preferably represents an alkali metal atom, such as sodium or potassium, or a quaternary ammonium or phosphonium ion.

Formula (VII) gives a general definition of the halogen compounds furthermore required as starting materials in process (d) according to the invention. In this formula, R preferably has the meanings which have already been mentioned for the substituents $R^1$ in connection with the description of the substances according to the invention, of the formula (I), with the exception of the meaning hydrogen. Hal preferably represents chlorine or bromine.

The halogen compounds of the formula (VII) are known or can be prepared by methods which are known in principle.

Suitable diluents for the first stage of process (a) according to the invention are inert organic solvents. They preferably include ethers such as tetrahydrofuran or dioxane, aliphatic and aromatic hydrocarbons, such as, in particular, benzene, toluene or xylene; and dimethylsulphoxide.

In carrying out the first stage of process (a) according to the invention, the reaction temperatures can be varied within a relatively wide range. In general the reaction is carried out at between 0° and 100° C., preferably between 10° and 60° C.

In carrying out the first stage of process (a) according to the invention, 1 to 3 mols of dimethyloxosulphonium methylide of the formula (III), produced in situ from trimethyloxosulphonium iodide in dimethyl sulphoxide and potassium tert.-butylate, are preferably employed per mol of aryl cyclopropyl ketone of the formula (II). The intermediate products of the formula (IV) are isolated in a generally customary manner.

Suitable diluents for the second stage of process (a) according to the invention are inert organic solvents. Those which are preferably used are nitriles, such as, in particular, acetonitrile; aromatic hydrocarbons, such as benzene, toluene and dichlorobenzene; formamides, such as, in particular, dimethylformamide; and hexamethylphosphoric acid triamide.

The second stage of process (a) according to the invention is carried out in the presence of a base. All inorganic and organic bases which are customarily used are suitable for this process. These preferably include alkali metal carbonates, such as, for example, sodium carbonate and potassium carbonate; alkali metal hydroxides, such as, for example, sodium hydroxide; alkali metal alcoholates, such as, for example, sodium methylate, potassium methylate, sodium ethylate and potassium ethylate; alkali metal hydrides, such as, for example, sodium hydride; and lower tertiary alkylamines, cycloalkylamines and aralkylamines, such as, in particular, triethylamine.

In carrying out the second stage of process (a) according to the invention, the reaction temperatures can be varied within a relatively wide range. In general, the reaction is carried out at temperatures between 0° C. and 200° C., preferably between 60° C. and 150° C.

In carrying out the second stage of process (a) according to the invention, 1 to 2 mols of the azole and 1 to 2 mols of the base are preferably employed per mol of the oxirane of the formula (IV). The end products are isolated in a generally customary manner.

The reaction conditions for carrying out process (b) according to the invention correspond to those for the procedure of the first stage of process (a).

In carrying out process (c) according to the invention, about 1 to 5 mols of oxidizing agent are employed per mol of the compounds according to the invention, of the formula (Ia). When 1 mol of oxidizing agent, such as m-chloroperbenzoic acid in methylene chloride or hydrogen peroxide in acetic acid or acetic anhydride, is used at temperatures between −30° C. and +30° C., the compounds according to the invention, of the formula (I), which contain the SO grouping are preferentially formed. With an excess of oxidizing agent and higher temperatures (10° to 80° C.), the compounds according to the invention, of the formula (I), which contain the —$SO_2$ grouping are preferentially formed. The oxidation products are isolated in a customary manner.

Suitable diluents for carrying out process (d) according to the invention are inert organic solvents. These preferably include ethers, such as diethyl ether or dioxane; aromatic hydrocarbons, such as benzene; in individual cases, also chlorinated hydrocarbons, such as chloroform, methylene chloride or carbon tetrachloride; and hexamethylphosphoric acid triamide.

In carrying out process (d) according to the invention, the reaction temperatures can be varied within a relatively wide range. In general, the reaction is carried out at between 0° and 120° C., preferably between 20° and 100° C.

In carrying out process (d) according to the invention, hydroxy compounds of the formula (Ib) are first reacted with strong bases to give the corresponding alcoholates of the formula (Ic). In the subsequent stage, 1 to 2 mols of the halogen compound of the formula (VII) are preferably employed per mol of an alcoholate of the formula (Ic).

To isolate the end products, the reaction mixture is freed from the solvent, and water and an organic solvent are added to the residue. The organic phase is separated off, worked up in the customary manner and purified.

In a preferred embodiment, the procedure is advantageously carried out as follows: the hydroxy compound of the formula (Ib) is used as a starting material, this compound, in a suitable organic solvent, is converted with an alkali metal hydride or alkali metal amide to the alkali metal alcoholate, and the latter, without being isolated, is reacted directly with the halogen compound of the formula (VII), the compounds according to the invention, of the formula (I), being obtained in one operation, with elimination of alkali metal halide.

In another preferred embodiment, the preparation of the alcoholates and the reaction with a halogen compound of the formula (VII) are advantageously carried out in a two-phase system, such as, for example, aqueous sodium hydroxide solution or potassium hydroxide solution/toluene or methylene chloride, with the addition of 0.01-1 mol of a phase-transfer catalyst, such as, for example, ammonium or phosphonium compounds, and reaction of the alcoholates with the halides present in the organic phase or takes place in the organic phase or at the boundary.

The acid addition salts of the compounds of the formula (I) can be obtained in a simple manner by customary salt formation methods, for example by dissolving a compound of the formula (I) in a suitable inert solvent, and adding the acid, for example hydrochloric acid, and can be isolated in a known manner, for example by filtration, and, if appropriate, purified by washing with an inert organic solvent.

The metal salt complexes of the compounds of the formula (I) can be obtained in a simple manner by customary processes, for example by dissolving the metal salt in alcohol, for example ethanol, and adding the solution to compounds of the formula (I). Metal salt complexes can be isolated in a known manner, for example by filtration, and, if appropriate, purified by recrystallization.

The active compounds which can be used according to the invention engage in the metabolism of the plants and can therefore be employed as growth regulators.

Experience to date of the mode of action of plant growth regulators has shown than an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging. In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soybeans or cereals. Using growth regulators it is also possible, for example, to inhibit the degradation of desired constituents, such as, for example, sugar in sugar beet or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds according to the invention also exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes, Deuteromycetes.

The good toleration, by plants, of the active compounds, at the concentrations required for combating plant diseases, permits treatment of above-ground parts of plants, of vegetative propagation stock and seeds, and of the soil. As plant protection agents, the active compounds according to the invention can be used with particularly good success for combating cereal and rice diseases and Venturia species, such as Venturia inaequalis. The substances according to the invention also possess a broad and good in vitro fungicidal action spectrum.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydro-carbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products. As dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When the compounds according to the invention are used as plant growth regulators, the amounts applied can be varied within a substantial range. In general, 0.01 to 50 kg, preferably 0.05 to 10 kg, are used per hectare of soil surface.

When the substances according to the invention are used as plant growth regulators, the rule is that they are applied within a preferred period of time, the exact definition of which depends on the climatic and vegetative circumstances.

When the substances according to the invention are used as fungicides, too, the amount applied can be varied within a substantial range, depending on the method of application. Thus, in the treatment of parts of plants, the active compound concentrations in the use forms are in general between 1 and 0.0001% by weight, preferably between 0.5 and 0.001% by weight. In the treatment of seed, amounts of active compound of 0.001 to 50 g per kg of seed, preferably 0.01 to 10 g, are generally required. In the treatment of the soil, active compound concentrations of 0.00001 to 0.1% by weight, preferably from 0.0001 to 0.02%, are required at the place of action.

The preparation and the use of the substances according to the invention can be seen from the examples which follow.

PREPARATION EXAMPLES

EXAMPLE 1

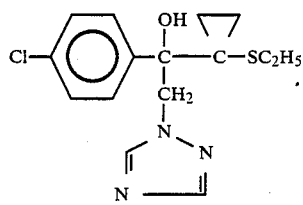 (I-1)

(Process a)
1st stage

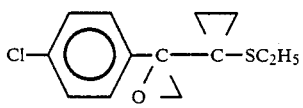 (IV-1)

170 ml of dry dimethyl sulphoxide are added dropwise to a mixture of 6.4 g of sodium hydride (80% strength) and 44.2 g of trimethylsulphoxonium iodide at 10° C., and stirring is continued for 1 hour at room temperature. Thereafter, 40 g (0.167 mol) of 1-(4-chlorobenzoyl)-1-ethylthio-cyclopropane in 50 ml of dimethylsulphoxide are added dropwise. The reaction mixture is stirred for two days at room temperature. Thereafter, it is poured onto 500 g of ice and extracted several times with ethyl acetate, and the combined organic phases are washed with water, dried over sodium sulphate and evaporated down. 40.5 g (95.5% of theory) of 1-[1-(4-chlorophenyl)-oxiranyl]1-ethylthio-cyclopropane are obtained as an oil, which is directly reacted further.

2nd stage

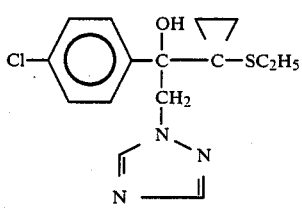 (I-1)

A solution of 40.5 g (0.16 mol) of 1-[1-(4-chlorophenyl)-oxiranyl]-1-ethylthio-cyclopropane (see Example IV-1) in 50 ml of acetonitrile is added dropwise to a boiling mixture of 33.5 g of 1,2,4-triazole and 22 g of potassium carbonate in 150 ml of acetonitrile, and the reaction mixture is heated for 8 hours under reflux. The mixture is allowed to cool, 400 ml of water are added, and the crystalline product is filtered off under suction. After the product has been recrystallized from ethanol/water, 26.5 g (51% of theory) of 1-(4-chlorophenyl)-1-[1-(ethylthio)-1-cyclopropyl]-2-(1,2,4-triazol-1-yl)1-ethanol of melting point 165° C. are obtained.

Preparation of the starting material

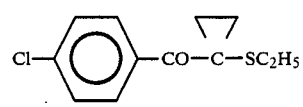 (II-1)

A solution of 38 g of potassium hydroxide in 250 ml of methanol is added dropwise at 0° C. to a solution of 100 g (0.338 mol) of 4-chlorophenyl 1-(bromo-3-chloropropyl) ketone and 21 g of ethylthiol in 200 ml of dimethylformamide. Stirring is continued for one hour at room temperature and for one hour under reflux. Thereafter, the mixture is evaporated down in vacuo, and the residue is taken up in a mixture of water and methylene chloride. The organic phase is separated off, washed with water, dried over sodium sulphate and evaporated down in vacuo. The residue is distilled in a high vacuum. 70.1 g (86% of theory) of 1-(4-chlorobenzoyl)-1-ethylthio-cyclopropane of boiling point b.p.$_{0.15}$=127° C. are obtained.

EXAMPLE 2

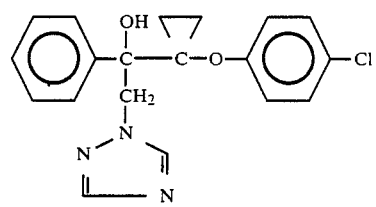 (I-2)

(Process b)

19.7 g (0.06 mol) of 1-(4-chlorophenoxy)-2-(1,2,4-triazol-1-yl)-propiophenone are introduced in portions into a solution of dimethylsulphoxonium methylide in 70 ml of dimethyl sulphoxide [prepared from 27.6 g (0.125 mol) of trimethylsulphoxonium iodide and 14.03 g (0.125 mol) of potassium tert.-butylate].

The mixture is stirred for 6 hours at 60° C. and then diluted with 1000 ml of water, the oil which separates out is taken up in chloroform, the solution is dried over sodium sulphate and evaporated down, and the residue is purified by chromatography (silica gel F 60 from Merck/mobile phase chloroform). The oil which remains crystallizes on stirring with acetonitrile. 1.7 g (8% of theory) of 1-(4-chlorophenoxy)-1-[1-hydroxy-1-phenyl-2-(1,2,4-triazol-1-yl)]-cyclopropane of melting point 170° C. are obtained.

Preparation of the precursor

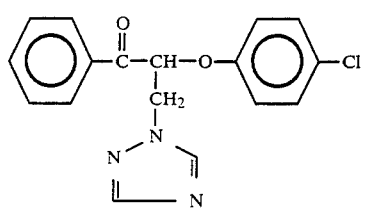

10.8 g (0.18 mol) of acetic acid and 1.8 ml (0.018 mol) of piperidine are added in succession to 29.4 g (0.12 mol) of ω-(4-chlorophenoxy)-acetophenone and 11.9 g (0.12 mol) of 1,2,4-triazol-1-yl-methyl-alcohol in 200 ml of toluene, and the mixture is boiled under a water separator until the amount of water which has been separated off remains constant. The toluene solution is then washed with water, dried over sodium sulphate and evaporated down, and the oily residue is purified by chromatography (silica gel F 60 from Merck/mobile phase chloroform). 20.8 g (53% of theory) of 1-(chlorophenoxy)-2-(1,2,4-triazol-1-yl)-propiophenone of melting point 126° C. are obtained.

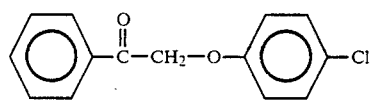

A solution of 154.6 g (1 mol) of α-chloroacetophenone in 250 ml of butanone is added dropwise to a boiling solution of 129 g (1 mol) of 4-chlorophenyl, 140 g (1 mol) of potassium carbonate and 2 g of potassium iodide in 800 ml of butanone, and, when the addition is complete, the mixture is boiled under reflux for a further 12 hours. The reaction mixture obtained is filtered and evaporated down. 179 g (73% of theory) of α-(4-chlorophenoxy)-acetophenone of melting point 97° C. are obtained.

EXAMPLE 3

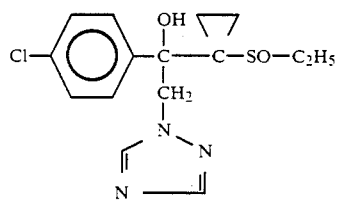

(Process c)

5 g (0.0155 mol) of 1-(4-chlorophenyl)-1-[1-(ethylthio)-1-cyclopropyl]-2-(1,2,4-triazol-yl)-1-ethanol (see Example 1) are stirred with 3.3 g of m-chloroperbenzoic acid (80–90% strength) in 40 ml of methylene chloride overnight at room temperature and then for one hour under reflux. Thereafter, the mixture is washed with twice 20 ml of 5% strength aqueous sodium hydroxide solution and twice with water. The organic phase is dried over sodium sulphate and evaporated down in vacuo. The residue is recrystallized from glycol monomethyl ether acetate. 3 g (57% of theory) of 1-(4-chlorophenyl)-1-[1-(ethylsulphinyl)-1-cyclopropyl]-2-(1,2,4-triazol-yl)1-ethanol of boiling point 185° C. are obtained.

EXAMPLE 4

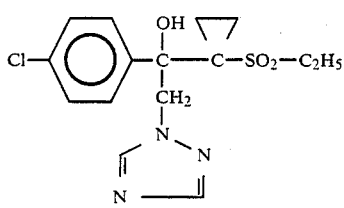

(Process c)

3.2 g (0.01 mol) of 1-(4-chlorophenyl)-1-([1-(ethylthio)-1-cyclopropyl]-2-(1,2,4-triazol-1-yl)-1-ethanol (see Example 1) are dissolved in 20 ml of glacial acetic acid, and the solution is stirred with 4 ml of 30% strength hydrogen peroxide for 6 hours at 70° C. Thereafter, 100 ml of ice water are added, the mixture is neutralized with concentrated aqueous sodium hydroxide solution, and the crystalline solid is filtered off under suction. 3.4 g (96% of theory) of 1-(4-chlorophenyl)[1-(ethylsulphonyl)-1-cyclopropyl]-2-(1,2,4-triazol-1-yl)1-ethanol of melting point 215° C. are obtained.

The substances of the formula (I) which are listed in Table 1 below, are also prepared by the methods described in the above examples and in accordance with the data for the processes according to the invention.

TABLE 1

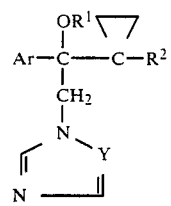

| Compound No. | Ar | R¹ | Y | R² | Melting point (°C.) |
|---|---|---|---|---|---|

TABLE 1-continued

| No. | Ar | R | X | Y | mp (°C) |
|---|---|---|---|---|---|
| I-5 | 4-Cl-C6H4- | H | N | -O-C6H5 | 139 |
| I-6 | " | " | " | -S-(CH2)3CH3 | 129 |
| I-7 | " | " | " | -SO2-(CH2)3CH3 | 136 |
| I-8 | " | " | " | F | 128 |
| I-9 | " | " | " | -O-(2,4-Cl2-C6H3) | 167 |
| I-10 | " | " | CH | -O-(4-Cl-C6H4) | 211 |
| I-11 | " | " | N | -S-(4-Cl-C6H4) | 137 |
| I-12 | C6H5- | " | " | -S-(2,5-Cl2-C6H3) | 161 |
| I-13 | 4-Cl-C6H4- | " | " | -S-CH2-(4-Cl-C6H4) | 183 |
| I-14 | 3,4-Cl2-C6H3- | H | N | -S-CH2-(4-Cl-C6H4) | — |
| I-15 | 4-biphenyl- | " | " | -O-C6H5 | 121 |
| I-16 | 4-Cl-C6H4- | " | " | -SCH3 | 124 |
| I-17 | " | " | CH | -SCH3 | 159 |
| I-18 | " | " | N | -SO2-CH3 | 193 |
| I-19 | " | " | " | -SO2-C2H5 | 185 |
| I-20 | " | " | CH | -S-C2H5 | 158 |
| I-21 | " | " | N | -S(CH2)2-CH3 | 131 |
| I-22 | " | " | CH | -S-(CH2)2-CH3 | 133 |
| I-23 | " | " | N | -S-CH2-CH=CH2 | 134 |
| I-24 | " | " | N | -S-C6H5 | 141–143 |

TABLE 1-continued

| No. | Ar | | X | R | mp |
|---|---|---|---|---|---|
| I-25 | " | | CH | —S—C₆H₅ | 145 |
| I-26 | 4-Cl-C₆H₄ | | N | —S—C₆H₄-Cl | 94 |
| I-27 | " | | " | CH | —O—C₆H₅ | 208 |
| I-28 | " | | N | —O—C₆H₄-Cl | 265 |
| I-29 | " | | " | " | —O—C₆H₄(Cl) (2-Cl) | 119 |
| I-30 | " | | " | " | —O—C₆H₃(Cl)₂ (2,4-diCl) | 181 |
| I-31 | " | | " | CH | —O—C₆H₃(Cl)₂ (2,4-diCl) | 213 |
| I-32 | " | | " | N | —N(piperazinyl)N—CH₃ | 122 |
| I-33 | 4-F-C₆H₄ | | H | N | F | 148 |
| I-34 | " | | " | " | —SCH₃ | 113 |
| I-35 | " | | " | CH | " | 156 |
| I-36 | 4-Cl-C₆H₄ | | H | N | —SC₂H₅ | 126 |
| I-37 | " | | " | CH | " | 161 |
| I-38 | 4-F-C₆H₄ | | H | N | —S—(CH₂)₃—CH₃ | 130 |
| I-39 | " | | " | CH | —S—(CH₂)₃—CH₃ | 140 |
| I-40 | 4-biphenyl | | " | N | —O—C₆H₄-Cl | |

TABLE 1-continued

| Compound | | | | Melting point [°C.] respectively |
|---|---|---|---|---|
| I-41 | 4-F-C6H4- | " | " | -O-C6H5 | 171 |
| I-42 | " | " | " | -O-C6H4-4-Cl | 144 |
| I-43 | " | " | CH | -O-C6H4-4-Cl | 184 |
| I-44 | " | " | N | -O-C6H3-2,4-Cl2 | 141 |
| I-45 | " | " | CH | -O-C6H3-2,4-Cl2 | 227 |
| I-46 | 4-F-C6H4- | H | N | -O-C6H4-2-Cl | 122 |
| I-47 | C6H5- | " | " | -SC2H5 | 137 |
| I-48 | " | " | CH | " | 179 |
| I-49 | " | " | N | -S-C6H4-4-Cl | 144 |
| I-50 | " | " | CH | -S-C6H4-4-Cl | 168 |
| I-51 | " | " | " | -O-C6H4-4-Cl | 177 |
| I-52 | " | " | " | -O-C6H3-2,4-Cl2 | 245 |
| I-53 | 4-biphenyl- | " | N | F | 123 |
| I-54 | " | " | " | -SCH3 | 163 |

TABLE 1-continued

| No. | Ar | R¹ | Y | R² | Refractive index [$n_D^{20}$] |
|---|---|---|---|---|---|
| I-55 | biphenyl | H | CH | —SCH₃ | 160 |
| I-56 | " | " | N | —SC₂H₅ | 159 |
| I-57 | " | " | CH | " | |
| I-58 | " | " | N | —S—(CH₂)₃—CH₃ | 136 |

| Compound No. | Ar | R¹ | Y | R² | Melting point [°C.] Refractive index [$n_D^{20}$] |
|---|---|---|---|---|---|
| I-62 | 2,4-dichlorophenyl | H | N | —S—C₄H₉-n | 86 |
| I-63 | 2-chlorophenyl | H | N | —S—C₄H₉-n | 1.5790 |
| I-64 | 2,4-dichlorophenyl | H | N | —S—CH₂—CH=C(CH₃)₂ | 1.5698 |
| I-65 | 2,4-dichlorophenyl | H | N | —S—C₃H₇-iso | 128 |
| I-66 | 2,4-difluorophenyl | H | N | —S—C₂H₅— | 110 |
| I-67 | 2-chlorophenyl | H | N | —S—CH₂—CH=C(CH₃)₂ | 1.5598 |
| I-68 | 2-fluoro-4-chlorophenyl | H | N | —S—C₃H₇₆ | 112 |
| I-69 | 2-chlorophenyl | H | N | —S—C₂H₅ | 1.5560 |
| I-70 | 2-chlorophenyl | H | N | —S—CH₂—C₃H₇-iso | 1.5700 |

TABLE 1-continued

| No. | Ar | X | Y | R | mp |
|---|---|---|---|---|---|
| I-71 | 2-Cl-phenyl | H | N | —S—(CH$_2$)$_5$—CH$_3$ | 1.5430 |
| I-72 | 4-Cl-phenyl | H | CH | F | 176 |
| I-73 | 4-Cl-phenyl | H | N | —SO$_2$—(4-Cl-phenyl) | 166 |
| I-74 | 4-Cl-phenyl | H | N | —CH(CH$_3$)—CH$_2$—CH$_3$ | 104 |
| I-75 | 4-Cl-phenyl | H | N | —CH(CH$_3$)$_2$ | 137 |
| I-76 | 4-Cl-phenyl | H | N | —CH$_2$—CH(CH$_3$)—CH$_3$ | 147 |
| I-77 | 4-Cl-phenyl | H | N | —(CH$_2$)$_5$—CH$_3$ | 130 |
| I-78 | 4-Cl-phenyl | H | N | —CH$_2$—CH$_2$—CH(CH$_3$)—CH$_3$ | 141 |
| I-79 | 4-Cl-phenyl | H | N | —SO—C$_4$H$_9$-n | oil |
| I-80 | 4-Cl-phenyl | H | N | —SO—C$_3$H$_7$-n | 146 |
| I-81 | 4-Cl-phenyl | H | N | —SO—CH$_2$—CH(CH$_3$)—CH$_3$ | 113 |
| I-82 | 4-Cl-phenyl | H | N | —O—(4-F-phenyl) | 147 |
| I-83 | 4-Cl-phenyl | H | N | —N(piperidinyl) | 130 |

TABLE 1-continued

| | | | | |
|---|---|---|---|---|
| I-84 | 4-Cl-C₆H₄ | H | N | —Cl | 149 |
| I-85 | 4-Cl-C₆H₄ | H | N | —S—(CH₂)₁₁—CH₃ | 111 |
| I-86 | 4-Cl-C₆H₄ | H | N | —SO(CH₂)₃—CH₃ | 153 |
| I-87 | 4-Cl-C₆H₄ | H | CH | —S—(cyclohexyl-H) | 191 |
| I-88 | 4-Cl-C₆H₄ | H | N | —S—(cyclohexyl-H) | 142 |
| I-89 | 4-Cl-C₆H₄ | H | N | —SO—(CH₂)₁₁—CH₃ | oil |
| I-90 | 4-Cl-C₆H₄ | H | N | —SO₂—(CH₂)₁₁—CH₃ | 91 |
| I-91 | 4-Cl-C₆H₄ | H | N | —S—CH₂—CH₂—O—(tetrahydropyran-2-yl) | 75 |
| I-92 | 4-Cl-C₆H₄ | H | N | —SO—CH₃ | 189 (1 diastereomer) |
| I-93 | 4-Cl-C₆H₄ | H | N | —SO—CH₃ | 172 (Mixture of diastereomers) |
| I-94 | 4-Cl-C₆H₄ | H | N | —SO₂—C₃H₇-n | 128 |
| I-95 | 4-Cl-C₆H₄ | H | N | —SO—CH(CH₃)—C₂H₅ | 117 |
| I-96 | 4-Cl-C₆H₄ | H | N | —SO₂—CH(CH₃)₂ | 159 |

TABLE 1-continued

| No. | Ar | R | X | Y | mp (°C) |
|---|---|---|---|---|---|
| I-97 | 4-Cl-C₆H₄- | H | N | —SO₂—CH₂—CH(CH₃)₂ | |
| I-98 | 4-Cl-C₆H₄- | H | N | —SO₂—(CH₂)₅—CH₃ | 140 |
| I-99 | 4-Cl-C₆H₄- | H | N | —SO₂—CH₂—CH₂—CH(CH₃)₂ | 165 |
| I-100 | 4-Cl-C₆H₄- | H | N | —SO₂—C₆H₁₁ | 176 |
| I-101 | 4-Cl-C₆H₄- | H | N | —S—CH₂—CH₂—S—C₂H₅ | 95 |
| I-102 | 4-Cl-C₆H₄- | H | N | —S—CH₂—COOCH₃ | 118 |
| I-103 | 4-Cl-C₆H₄- | H | N | —S—CH₂—CH₂—OH | 138 |
| I-104 | 4-F-C₆H₄- | H | N | —SO—(CH₂)₃—CH₃ | 81 |
| I-105 | 4-F-C₆H₄- | H | CH | —S—CH(CH₃)₂ | 191 |
| I-106 | 4-F-C₆H₄- | H | N | —S—CH(CH₃)₂ | 155 |
| I-107 | 4-F-C₆H₄- | H | N | —Cl | 121 |
| I-108 | 4-biphenylyl | H | N | —SO₂CH₃ | 162 |
| I-109 | C₆H₅- | H | N | —S—CH(CH₃)₂ | 136 |

TABLE 1-continued
| | | | | | |
|---|---|---|---|---|---|
| I-110 | 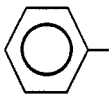 | H | CH | —F | 162 |
| I-111 | 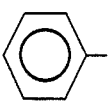 | H | N | —F | 105 |
| I-112 | 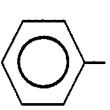 | H | N | —SCH$_3$ | 108 |
| I-113 | 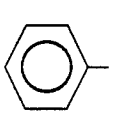 | H | CH | —SCH$_3$ | 167 |
| I-114 | 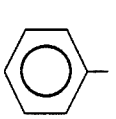 | H | CH | —S—C$_4$H$_9$-n | 134 |
| I-115 | 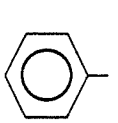 | H | N | —S—C$_4$H$_9$-n | 125 |
| I-116 | 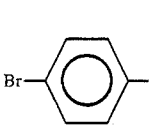 | H | N | —F | 123 |
| I-117 | 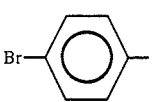 | H | N | —SC$_2$H$_5$ | 168 |
| I-118 | 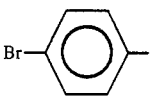 | H | N | —Cl | 127 |
| I-119 |  | H | N | —SCH$_3$ | 127 |
| I-120 | 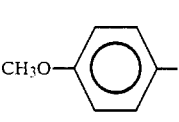 | H | N | —F | 111 |
| I-121 | 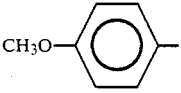 | H | N | —SC$_2$H$_5$ | 119 |
| I-122 | 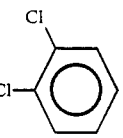 | H | N | 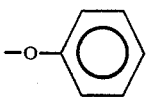 | 139 |

TABLE 1-continued

| Compound No. | Ar | R¹ | Y | R² | Melting point [°C.] respective Refractive index [$n_D^{20}$] |
|---|---|---|---|---|---|
| I-123 | 3,4-diCl-phenyl | H | N | —S—C₄H₉-n | 170 |
| I-124 | 3,4-diCl-phenyl | H | N | —SO—C₄H₉-n | resin |
| I-125 | 3,4-diCl-phenyl | H | N | —SO₂—C₄H₉-n | 159 |
| I-126 | 3,4-diCl-phenyl | H | N | —SCH₃ | 142 |
| I-127 | 3,4-diCl-phenyl | H | N | —SO₂CH₃ | |
| I-128 | 3,4-diCl-phenyl | H | N | —S—CH₂—CH₂—CH₃ | |
| I-129 | 3,4-diCl-phenyl | H | N | —S—C₂H₅ | |
| I-130 | 3,4-diCl-phenyl | H | N | —S—CH(CH₃)₂ | |

| Compound No. | Ar | R¹ | Y | R² | Melting point [°C.] respective Refractive index [$n_D^{20}$] |
|---|---|---|---|---|---|
| I-131 | 2,4-diF-phenyl | H | N | —S—CH₃ | 83 |
| I-132 | 2,4-diF-phenyl | H | N | —SO₂CH₃ | |
| I-133 | 2,4-diF-phenyl | H | N | —Cl | |

TABLE 1-continued
| | | | | |
|---|---|---|---|---|
| I-134 | 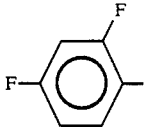 2,4-difluorophenyl | H | N | —O—phenyl |
| I-135 | 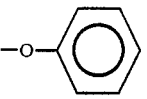 4-CH₃-phenyl | H | N | —F | 127 |
| I-136 | 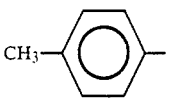 4-CH₃-phenyl | H | N | —SC₂H₅ | 125 |
| I-137 | 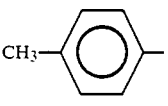 4-CH₃-phenyl | H | N | —O—phenyl | 146 |
| I-138 | 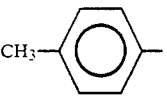 4-CH₃-phenyl | H | N | —SCH₃ | |
| I-139 | 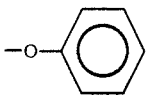 4-CH₃-phenyl | H | N | —S—CH(CH₃)₂ | |
| I-140 | 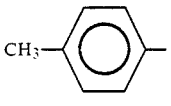 4-CH₃-phenyl | H | N | —S—CH₂—CH₂—CH₃ | |
| I-141 | 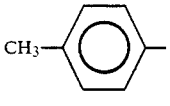 4-CH₃-phenyl | H | N | —S—CH₂—CH(CH₃)₂ | |
| I-142 | 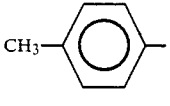 4-CH₃-phenyl | H | N | —S—(CH₂)₃—CH₃ | |
| I-143 | 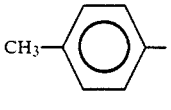 4-F-phenyl | H | N | —SO₂CH₃ | 189 |
| I-144 | 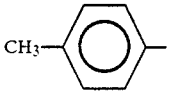 4-F-phenyl | H | N | —SO₂—CH(CH₃)₂ | 177 |
| I-145 | 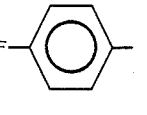 4-F-phenyl | H | N | —SO—CH(CH₃)₂ | 141 |
| I-146 | 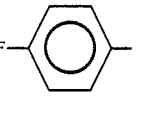 4-Cl-phenyl | H | CH | —F | 176 |

TABLE 1-continued

| Compound No. | Ar | R¹ | Y | R² | Melting point [°C.] |
|---|---|---|---|---|---|
| I-147 | 4-Cl-C₆H₄ | H | N | —SO—CH₃ | 189 |
| I-148 | 2,4-F₂-C₆H₃ | H | N | —Cl | 109 |
| I-149 | 2,4-F₂-C₆H₃ | H | N | —O—C₆H₅ | 133 |
| I-150 | 3,4-Cl₂-C₆H₃ | H | N | —SO₂—(CH₂)₂—CH₃ | 104 |
| I-151 | 3,4-Cl₂-C₆H₃ | H | N | —SO—(CH₂)₂—CH₃ | 140 |
| I-152 | 3,4-Cl₂-C₆H₃ | H | N | —SO₂—CH₂—CH₃ | 135 |
| I-153 | 3,4-Cl₂-C₆H₃ | H | N | —SO₂—CH₂—CH₃ | 112 |
| I-154 | 3,4-Cl₂-C₆H₃ | H | N | —SO₂—CH(CH₃)₂ | 137 |
| I-155 | 3,4-Cl₂-C₆H₃ | H | N | —SO—CH(CH₃)₂ | 131 |
| I-156 | 3,4-Cl₂-C₆H₃ | H | N | —SO₂—CH₃ | 160 |
| I-157 | 4-CH₃-C₆H₄ | H | N | —F | 127 |

TABLE 1-continued
| I-158 | 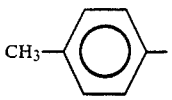 | H | N | —S—CH$_2$—CH$_3$ | 125 |
| I-159 | 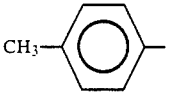 | H | N | —S—CH$_3$ | 116 |
| I-160 | 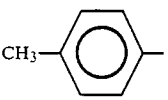 | H | N | —SO$_2$—CH(CH$_3$)$_2$ | 149 |
| I-161 | 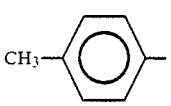 | H | N | —SO—CH(CH$_3$)$_2$ | 127 |
| I-162 | 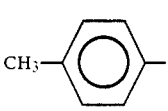 | H | N | —S—(CH$_2$)$_2$—CH$_3$ | 115 |
| I-163 | 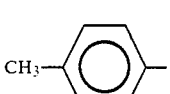 | H | N | —S—CH$_2$—CH(CH$_3$)$_2$ | 123 |
| I-164 | 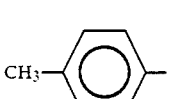 | H | N | —S—(CH$_2$)$_3$—CH$_3$ | 107 |
| I-165 | 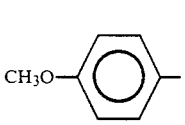 | H | N | —F | 111 |
| I-166 | 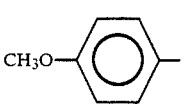 | H | N | —S—CH$_2$—CH$_2$ | 119 |
| Compound No. | Ar | R$^1$ | Y | R$^2$ | Melting point [°C.] resp. Refractive index [n$_D^{20}$] |
|---|---|---|---|---|---|
| I-167 | 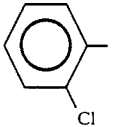 | H | N | 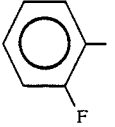 | 1.5630 |
| I-168 | 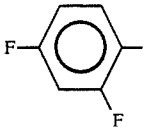 | H | N | —SC$_3$H$_7$ | 75 |
| I-169 |  | H | N | —SC$_4$H$_9$ | 75 |

TABLE 1-continued

| No. | Aryl | R | X | Substituent | Value |
|---|---|---|---|---|---|
| I-170 | 2-Cl-C₆H₄ | H | N | —S—CH(CH₃)₂ | 1.5630 |
| I-171 | 2-Cl-C₆H₄ | H | N | —S—C(CH₃)₃ | 1.5660 |
| I-172 | 2-Cl-C₆H₄ | H | N | —S—CH(CH₃)—C₂H₅ | 1.5582 |
| I-173 | 3,4-F₂-C₆H₃ | H | N | —S—CH(CH₃)₂ | 106 |
| I-174 | 3-Cl-C₆H₄ | H | N | —S—C₃H₇ | 110 |
| I-175 | 3,4-F₂-C₆H₃ | H | N | —S—C₃H₇ | 1.5420 |
| I-176 | 3-F-4-Cl-C₆H₃ | H | N | —S—CH(CH₃)₂ | 118 |
| I-177 | 2-F-C₆H₄ | H | N | —S—CH(CH₃)₂ | 80 |

FURTHER EXAMPLES OF THE PREPARATION OF STARTING MATERIALS OF THE FORMULA (II)

EXAMPLE (II-2)

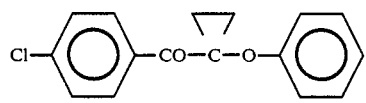
(II-2)

14 g of potassium carbonate are added to a solution of 29.6 g (0.1 mol) of 4-chlorophenyl 1-bromo-3-chloropropyl ketone and 9.4 g of phenol in 60 ml of dimethylformamide, and the mixture is heated to 50° C. for 3 hours. Thereafter, 8.4 g of potassium hydroxide in 40 ml of methanol are added dropwise at room temperature, and the mixture is heated to 60° C. for 3 hours. The mixture is evaporated down in vacuo, and the residue is taken up in a water/methylene chloride mixture. The organic phase is separated off, washed with water, dried over sodium sulphate and evaporated down in vacuo. The residue is distilled in a high vacuum. 20.7 g (76.1% of theory) of 1-(4-chlorobenzoyl)-1-phenoxycyclopropane of boiling point b.p.$_{0.15}$=170°–180° C. are obtained.

EXAMPLE (II-3)

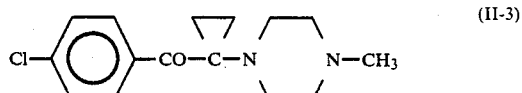
(II-3)

A solution of 29.6 g (0.1 mol) of 4-chlorophenyl 1-bromo-3-chloropropyl ketone in 30 ml of dimethylformamide is added dropwise to a mixture of 10.4 g of N-methyl piperazine and 14 g of potassium carbonate in 30 ml of dimethylformamide at room temperature. Stirring is continued for 3 hours, after which a solution of 9 g of potassium hydroxide in 30 ml of methanol is added dropwise. The reaction mixture is stirred for a further hour at 50° C. and evaporated down in vacuo. The residue is taken up in ethyl acetate/water, and the organic phase is separated off, washed with water, dried over sodium sulphate and evaporated down in vacuo. The residue is chromatographed over silica gel using chloroform/ethanol (97:3). 14 g (50.3% of theory) of 1-(4-chlorobenzoyl)-1-(4-methylpiperazin-1-yl)-cyclopropane are obtained as a reddish oil, which can be directly used further.

EXAMPLE (II-4)

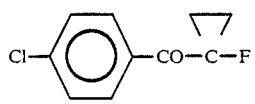

(II-4)

20 g (0.085 mol) of 4-chlorophenyl 1-fluoro-3-chloropropyl ketone are dissolved in 150 ml of tert.-butanol, and 15 g of potassium tert.-butylate are added in portions. Stirring is continued for 2 hours at 40° C., and the mixture is evaporated down in vacuo. The residue is taken up in methylene chloride and water. The organic phase is separated off, dried over sodium sulphate and evaporated down in vacuo. The residue is distilled in a high vacuum. 14.4 g (85% of theory) of 1-(4-chlorobenzoyl)-1-fluoro-cyclopropane of boiling point b.p.$_{0.1}$=75° C. are obtained.

Preparation of starting materials of the formula (VIII)

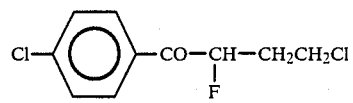

(VIII-1)

A mixture of 68 g of 4-chlorophenyl 1-bromo-3-chloropropyl ketone, 27.5 g of dry potassium fluoride, 11 g of 18-crown-6 and 200 ml of dry benzene is heated under reflux for 8 hours. Thereafter, 200 ml of water are added, and the organic phase is separated off, washed several times with water, dried over sodium sulphate and evaporated down in vacuo. The residue is stirred with light benzine, with the addition of a small amount of toluene. After the resulting solid has been filtered off under suction and drying has been carried out, 28.5 g (53% of theory) of 4-chlorophenyl 1-fluoro-3-chloropropyl ketone of melting point 53° C. are obtained.

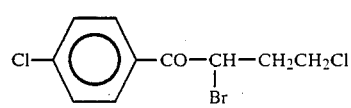

(VIII-2)

A solution of 358 g of bromine in 350 ml of methylene chloride is added dropwise to a solution of 483 g (2.23 mols) of 4-chlorophenyl 3-chloropropyl ketone in 1200 ml of methylene chloride at 20° C. Stirring is continued for one hour and the mixture is then evaporated down in vacuo. 300 ml of petroleum ether are added to the residue, and stirring is continued until crystallization is complete. The mixture is cooled to 10° C., and the precipitate is filtered off under suction. 582 g (88.3% of theory) of 4-chlorophenyl 1-bromo-3-chloropropyl ketone of melting point 73° C. are obtained.

The precursors of the formula (II) which are listed in Table 2 below are also prepared analogously to the methods described in Examples (II-1) to (II-4) and under the stated process conditions.

TABLE 2

Ar—CO—C—R$^2$ (with cyclopropane ring on C)  (II)

| Example No. | Ar | R$^2$ | Physical constant |
|---|---|---|---|
| II-5 | Cl—⌬— | —S—(CH$_2$)$_3$CH$_3$ | B.p.$_{0.1}$ = 133° C. |
| II-6 | Cl—⌬— | —S—CH$_3$ | B.p.$_{0.1}$ = 120° C. |
| II-7 | Cl—⌬— | —C(CH$_3$)$_3$ | viscous oil |
| II-8 | Cl—⌬— | —O—⌬—Cl | B.p.$_{0.1}$ = 160° C. |

TABLE 2-continued $$Ar-CO-C-R^2 \quad \text{(II)}$$
(with cyclopropyl on C)

| Example No. | Ar | R² | Physical constant |
|---|---|---|---|
| II-9 | 4-Cl-C₆H₄- | -O-(2,4-Cl₂-C₆H₃) | B.p.₀.₁ = 173° C. |
| II-10 | C₆H₅- | -O-(4-Cl-C₆H₄) | B.p.₀.₁ = 143° C. |
| II-11 | C₆H₅- | -O-(2,4-Cl₂-C₆H₃) | B.p.₀.₁ = 146° C. |
| II-12 | C₆H₅- | -S-(4-Cl-C₆H₄) | M.p. = 86° C. |
| II-13 | 4-biphenylyl | -SCH₃ | M.p. = 98° C. |
| II-14 | 4-F-C₆H₄- | -SCH₃ | B.p.₀.₁ = 102° C. |
| II-15 | 4-F-C₆H₄- | -O-C₆H₅ | B.p.₀.₁ = 125–130° C. |
| II-16 | 4-F-C₆H₄- | -O-(4-Cl-C₆H₄) | B.p.₀.₁ = 145–150° C. |
| II-17 | 4-F-C₆H₄- | -O-(2,4-Cl₂-C₆H₃) | B.p.₀.₁ = 165–173° C. |
| II-18 | 4-F-C₆H₄- | -S-C₂H₅ | B.p.₀.₀₇ = 95° C. |
| II-19 | 4-F-C₆H₄- | -S-(CH₂)₃CH₃ | B.p.₀.₁ = 113–116° C. |
| II-20 | 4-biphenylyl | -S-C₂H₅ | M.p. = 86° C. |

TABLE 2-continued $$Ar-CO-C-R^2 \quad \text{(II)}$$
(with cyclopropyl on C)

| Example No. | Ar | R² | Physical constant |
|---|---|---|---|
| II-21 | biphenyl-4-yl | —O—C₆H₅ | M.p. = 77° C. |
| II-22 | 4-F-C₆H₄— | —O-(2-Cl-C₆H₃)— | B.p.₀.₁ = 147–155° C. |
| II-23 | 4-Cl-C₆H₄— | —O-(2-Cl-C₆H₃)— | B.p.₀.₀₇ = 154° C. |
| II-24 | 4-Cl-C₆H₄— | —S—C₆H₅ | B.p.₀.₁ = 163–170° C. |
| II-25 | 4-Cl-C₆H₄— | —S-(4-Cl-C₆H₄) | M.p. = 104° C. |
| II-26 | 4-Cl-C₆H₄— | —S—CH₂—CH=CH₂ | B.p.₀.₀₆ = 122° C. |
| II-27 | 4-Cl-C₆H₄— | —C₃H₇-n | B.p.₀.₁₅ = 118° C. |
| II-28 | 4-F-C₆H₄— | F | B.p.₀.₀₇ = 55° C. |
| II-29 | biphenyl-4-yl | F | B.p.₀.₁₅ = 138° C./m.p. 73° C. |
| II-30 | 4-CH₃-C₆H₄— | F | B.p.₀.₁ = 69° C. |
| II-31 | 4-CH₃O-C₆H₄— | F | B.p.₀.₁ = 98° C. |
| II-32 | 4-Br-C₆H₄— | F | B.p.₀.₁ = 88° C. |

The intermediate products of the formula (IV) which are listed in Table 3 below are also prepared by the method described in Example 1 and under the stated process conditions.

TABLE 3

$$\text{Ar}-\underset{O}{\overset{\triangledown}{C}}-\overset{\triangle}{C}-R^2 \qquad (IV)$$

| Example No. | Ar | $R^2$ | Physical constant |
|---|---|---|---|
| IV-2 | 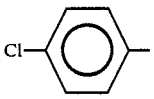 | 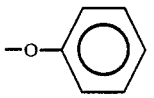 | viscous oil |
| IV-3 | 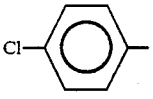 | —S—(CH$_2$)$_3$CH$_3$ | viscous oil |
| IV-4 |  | F | B.p.$_{0.2}$ = 83° C. |
| IV-5 |  | —SCH$_3$ | oil |
| IV-6 |  | —SC$_2$H$_5$ | oil |
| IV-7 |  | —S—(CH$_2$)$_3$—CH$_3$ | oil |
| IV-8 |  | —S—CH$_2$—CH=CH$_2$ | oil |
| IV-9 |  | —S—(CH$_2$)$_2$—CH$_3$ | oil |
| IV-10 | 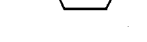 | 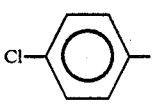 | oil |
| IV-11 | 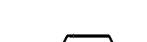 |  | oil |
| IV-12 |  | 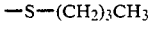 | oil |

TABLE 3-continued $$Ar-\underset{\underset{O}{\triangle}}{C}-\underset{\triangle}{C}-R^2 \quad (IV)$$

| Example No. | Ar | R² | Physical constant |
|---|---|---|---|
| IV-13 | 4-Cl-C₆H₄- | -O-C₆H₄-4-Cl | oil |
| IV-14 | 4-Cl-C₆H₄- | -O-C₆H₃-2,4-Cl₂ | M.p. 81° C. |
| IV-15 | 4-Cl-C₆H₄- | -O-C₆H₄-2-Cl | M.p. 97° C. |
| IV-16 | 4-Cl-C₆H₄- | F | B.p.₀.₂ = 83° C. |
| IV-17 | 4-Cl-C₆H₄- | -N(piperazinyl)N-CH₃ | oil |
| IV-18 | 4-F-C₆H₄- | -SCH₃ | oil |
| IV-19 | 4-F-C₆H₄- | -SC₂H₅ | oil |
| IV-20 | 4-F-C₆H₄- | -S-(CH₂)₃-CH₃ | oil |
| IV-21 | 4-F-C₆H₄- | -O-C₆H₅ | oil |
| IV-22 | 4-F-C₆H₄- | -O-C₆H₄-4-Cl | oil |
| IV-23 | 4-F-C₆H₄- | -O-C₆H₃-2,4-Cl₂ | M.p. 72° C. |

TABLE 3-continued
$$Ar-\underset{O}{\underset{\triangle}{C}}-\underset{\triangle}{\overset{\triangledown}{C}}-R^2 \quad (IV)$$
| Example No. | Ar | R² | Physical constant |
|---|---|---|---|
| IV-24 | 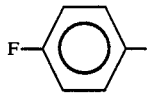 | 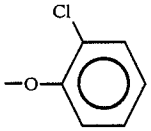 | oil |
| IV-25 | 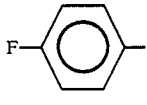 | F | oil |
| IV-26 | 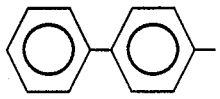 | —SCH₃ | oil |
| IV-27 |  | —SC₂H₅ | oil |
| IV-28 | 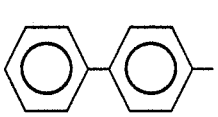 | —S—(CH₂)₃—CH₃ | oil |
| IV-29 | 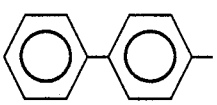 | 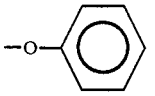 | M.p. 94° C. |
| IV-30 | 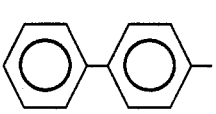 |  | M.p. 91° C. |
| IV-31 | 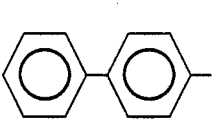 | F | oil |
| IV-32 | 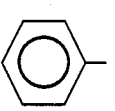 | —SC₂H₅ | oil |
| IV-33 | 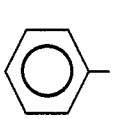 |  | oil |
| IV-34 | 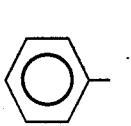 |  | oil |

TABLE 3-continued $$Ar-\underset{O}{\overset{\triangledown}{\underset{\triangle}{C-C-R^2}}}$$ (IV)

| Example No. | Ar | R² | Physical constant |
|---|---|---|---|
| IV-35 | 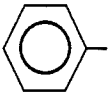 | 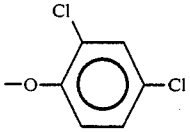 | M.p. 62° C. |

The intermediate products of the formula (VI) which are listed in Table 4 below are obtained in accordance with Example 2 and under the stated process conditions:

TABLE 4

$$Ar-\overset{O}{\overset{\|}{C}}-\underset{\underset{\underset{\|}{Y}\diagdown\underset{N}{N}\diagup}{\overset{|}{CH_2}}}{CH-R^2}$$ (VI)

| Example No. | Ar | Y | R² | Physical constant |
|---|---|---|---|---|
| VI-2 | 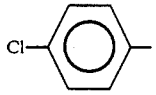 | N | 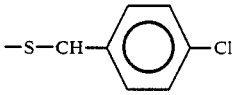 | M.p. 102° C. |
| VI-3 | 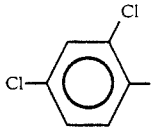 | N | 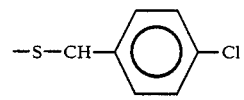 | M.p. 69° C. |
| VI-4 | 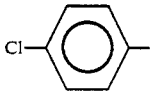 | N | 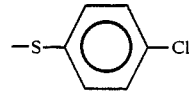 | M.p. 102° C. |
| VI-5 | 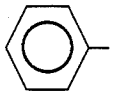 | N | 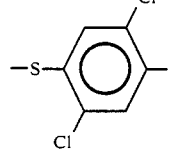 | M.p. 117° C. |
| VI-6 | 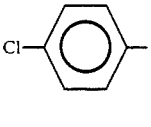 | N | 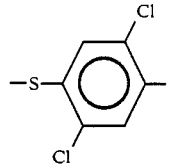 | M.p. 148° C. |
| VI-7 | 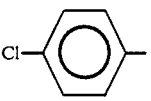 | CH | 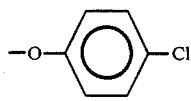 | M.p. 153° C. |

TABLE 4-continued
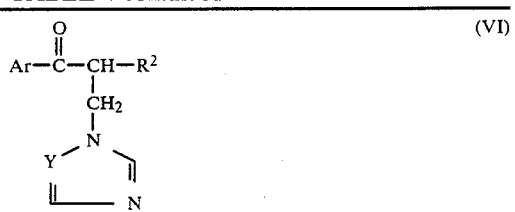
(VI)
| Example No. | Ar | Y | R² | |
|---|---|---|---|---|
| VI-8 | 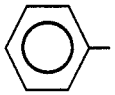 | N | 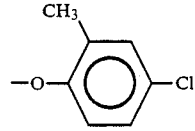 | M.p. 139° C. |
| VI-9 | 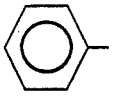 | N | 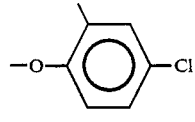 | M.p. 156° C. |
| VI-10 | 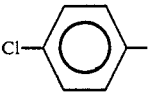 | N | 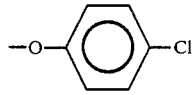 | M.p. 128° C. |
| | | | | Melting point [°C.] Refractive index [$n_D^{20}$] |
|---|---|---|---|---|
| VI-11 | 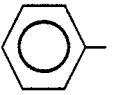 | N | 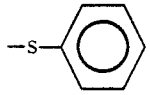 | 102 |
| VI-12 | 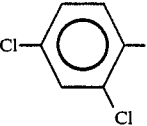 | N | —S—C₂H₅ | 50 |
| VI-13 | 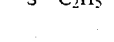 | N | —S—C₃H₇ | 1,5632 |
| VI-14 | 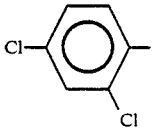 | N | —S—C₂H₅ | 62 |
| VI-15 |  | N | —S—C₃H₇ | 58 |
| VI-16 | 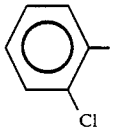 | N | —S—C₄H₉ | 1,5742 |

TABLE 4-continued

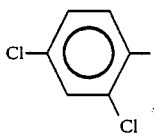

| Example No. | Ar | Y | R² | |
|---|---|---|---|---|
| V-17 | (2,4-dichlorophenyl) | N | —S—CH(CH₃)₂ | 1,5762 |

USE EXAMPLES

The compounds given below are employed as comparative substances in the following use examples:

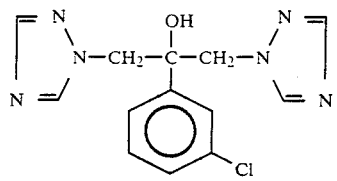

(A)

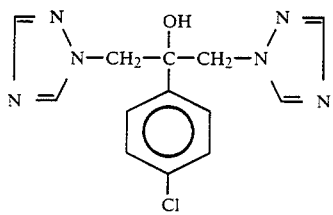

(B)

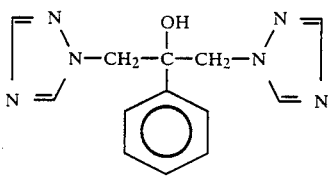

(C)

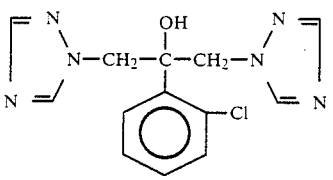

(D)

(disclosed in EP-OS (European Published Specification) No. 0,044,605).

EXAMPLE A

Inhibition of growth of rice

Solvent: 30 parts by weight of dimethylformamide
Emulsifier: 1 part by weight of polyoxyethylene sorbitan monolaurate.

To prepare a suitable preparation of active compound, 1 part by weight of active compound is mixed with the stated amounts of solvent and emulsifier, and the mixture is made up to the desired concentration with water.

Rice is grown in climatic chambers in small pots containing vermiculite, until the first leaf reaches a size of 1-2 cm. At this stage, the pots are placed in the prepared active compound solutions to a height corresponding to half the height of the pot.

After the development of the third leaf, the length of all plants is determined, and expressed as a percentage of the length of the control plants. 100% means growth corresponding to that of the control plants, values below 100% mean inhibition of growth, and values above 100% mean promotion of growth.

In this test, the active compounds (I-1), (I-6), (I-3) and (I-5), according to the invention exhibit pronounced inhibition of growth.

EXAMPLE B

Inhibition of growth of cotton

Solvent: 30 parts by weight of dimethylformamide
Emulsifier: 1 part by weight of polymethylene sorbitan monolaurate.

To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 3 weeks, the additional growth of the plants is measured and the inhibition of growth in per cent of the additional growth of the control plants is calculated. 100% inhibition of growth means that growth has stopped and 0% denotes a growth corresponding to that of the control plants.

In this test, the active compounds (I-4), (I-3) and (I-5) according to the invention exhibit more pronounced inhibition of growth than the compound (A) known from the prior art.

EXAMPLE C

Inhibition of growth of soya beans

Solvent: 30 parts by weight of dimethylformamide
Emulsifier: 1 part by weight of polyoxyethylene sorbitan monolaurate.

To produce a suitable preparation of active compound, 1 part by weight of active compound is mixed with the stated amounts of solvent and emulsifier and the mixture is made up to the desired concentration with water.

Soya bean plants are grown in a greenhouse until the first secondary leaf has unfolded completely. In this stage, the plants are sprayed with the preparations of active compound until dripping wet. After 3 weeks, the additional growth is measured on all the plants and the inhibition of growth in per cent of the additional growth of the control plants is calculated. 100% inhibition of growth means that growth has stopped and 0% denotes a growth corresponding to that of the control plants.

In this test, the active compounds (I-4) and (I-3) according to the invention exhibit more pronounced inhibition of growth than the compound (D) known from the prior art.

EXAMPLE D

Inhibition of growth of barley

Solvent: 30 parts by weight of dimethylformamide
Emulsifier: 1 part by weight of polyoxyethylene sorbitan monolaurate.

To produce a suitable preparation of active compound, 1 part by weight of active compound is mixed with the stated amounts of solvent and emulsifier and the mixture is made up to the desired concentration with water.

Barley plants are grown in a greenhouse to the 2-leaf stage. In this stage, the plants are sprayed with the preparations of active compound until dripping wet. After 3 weeks, the additional growth is measured on all plants and the inhibition of growth in per cent of the additional growth of the control plants is calculated. 100% inhibition of growth means that growth has stopped and 0% denotes a growth corresponding to that of the control plants.

In this test, the active compounds (I-4), (I-3) and (I-5) according to the invention exhibit more pronounced inhibition of growth than the compounds (A), (B), (C) and (D) known from the prior art.

EXAMPLE E

Venturia test (apple)/protective/

Solvent: 4.7 parts by weight of acetone
Emulsifier: 0.3 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, the compound (I-1) according to the invention shows a better activity than the known comparative substance (c).

It will be understood that the specification and examples are illustrative but not limitative of the present invention and that other embodiments within the spirit and scope of the invention will suggest themselves to those skilled in the art.

What is claimed is:

1. A substituted azolylmethyl-cyclopropyl-carbinol derivative of the formula

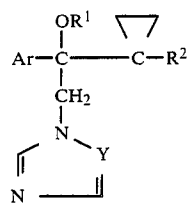

in which
Ar represents phenyl which is optionally monosubstituted or disubstituted by identical or different substituents selected from the group consisting of fluorine, chlorine, methyl, isopropyl, tert.-butyl, methoxy, methylthio, trifluoromethyl, trifluoromethoxy, trifluoromethylthio, and phenyl or phenoxy, each of which is optionally substituted by flourine, chlorine and/or methyl;
$R^2$ represents fluorine, chlorine, bromine, —X—$R^3$ or —$NR^4R^5$,
wherein
$R^3$ represents straight-chain or branched alkyl having 1 to 12 carbon atoms, cycloalkyl having 5 to 7 carbon atoms, straight-chain or branched alkenyl having 2 to 12 carbon atoms, hydroxyalkyl having 1 to 12 carbon atoms, alkylthioalkyl having 1 to 4 carbon atoms in the alkylthio part and 1 to 4 carbon atoms in the alkyl part, alkoxycarbonylalkyl having 1 to 4 carbon atoms in the alkyl part, and phenyl or benzyl, each of which is optionally monosubstituted or disubstituted by identical or different substituents selected from the group consisting of fluorine, chlorine, methyl, isopropyl, tert.-butyl, methoxy, methylthio, trifluoromethyl, trifluoromethoxy, trifluoromethylthio, and phenyl or phenoxy, each of which is optionally substituted by fluorine, chlorine and/or methyl; or
$R^3$ represents the radical of the formula

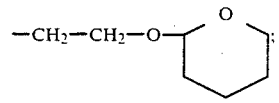

$R^4$ and $R^5$ together with the nitrogen atom to which they are bonded represent piperidinyl, piperazinyl or morpholinyl, each of which is optionally substituted by methyl, ethyl, methylcarbonyl or ethylcarbonyl, and
X represents oxygen, sulphur, and SO group or an $SO_2$ group, and
Y represents nitrogen,
or an addition product thereof with an acid or metal salt.

2. A substituted azolylmethyl-cyclopropyl-carbinol derivative according to claim 1 of the formula

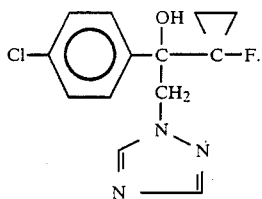

3. A plant growth-regulating or fungicidal composition comprising a plant growth-regulating or fungicidally effective amount of a compound or addition product according to claim 1 in admixture with an inert diluent.

4. A method of regulating the growth of plants which comprises applying to such plants, or to a locus in which said plants are grown or to be grown a plant growth-regulating effective amount of a compound or addition product according to claim 1.

5. A method of combating fungi which comprises applying to such fungi or to a habitat thereof a fungicidally effective amount of a compound or addition product according to claim 4.

* * * * *

UNITED STATES PATENT AND TRADEMARK OFFICE
CERTIFICATE OF CORRECTION

PATENT NO. : 4,921,528

DATED : May 1, 1990

INVENTOR(S) : Bockmann et aL.

It is certified that error appears in the above-identified patent and that said Letters Patent is hereby corrected as shown below:

Col. 68, claim 1 line 13   In formula delete " $OR^1$ " and substitute -- OH --

Signed and Sealed this

Seventeenth Day of March, 1992

Attest:

HARRY F. MANBECK, JR.

*Attesting Officer*   Commissioner of Patents and Trademarks